United States Patent
Ionescu et al.

(10) Patent No.: US 11,718,842 B2
(45) Date of Patent: Aug. 8, 2023

(54) ENCAPSULATED MICROORGANISMS AND METHODS OF USING SAME

(71) Applicant: LAVIE BIO LTD., Rehovot (IL)

(72) Inventors: Michael Ionescu, Mazkeret Batya (IL); Galit Kuznets, Tel Aviv (IL); Amir Bercovitz, Raanana (IL); Yossi Singer, Chashmonaim (IL); Hagai Karchi, Sitriya (IL)

(73) Assignee: LAVIE BIO LTD., Rehovot (IL)

( * ) Notice: Subject to any disclaimer, the term of this patent is extended or adjusted under 35 U.S.C. 154(b) by 60 days.

(21) Appl. No.: 17/260,293

(22) PCT Filed: Jul. 24, 2019

(86) PCT No.: PCT/IL2019/050838
§ 371 (c)(1),
(2) Date: Jan. 14, 2021

(87) PCT Pub. No.: WO2020/021549
PCT Pub. Date: Jan. 30, 2020

(65) Prior Publication Data
US 2021/0292738 A1    Sep. 23, 2021

Related U.S. Application Data

(60) Provisional application No. 62/702,917, filed on Jul. 25, 2018.

(51) Int. Cl.
| | | |
|---|---|---|
| C12N 11/04 | (2006.01) | |
| C12N 11/084 | (2020.01) | |
| A01N 25/28 | (2006.01) | |
| C12N 1/04 | (2006.01) | |
| C12N 1/20 | (2006.01) | |

(52) U.S. Cl.
CPC .............. *C12N 11/04* (2013.01); *A01N 25/28* (2013.01); *C12N 1/04* (2013.01); *C12N 1/20* (2013.01); *C12N 11/084* (2020.01)

(58) Field of Classification Search
CPC .......... C12N 1/20; C12N 1/04; C12N 11/084; C12N 11/04; A01N 25/28
See application file for complete search history.

(56) References Cited

U.S. PATENT DOCUMENTS

| | | | | |
|---|---|---|---|---|
| 7,422,737 B1 * | 9/2008 | Nussinovitch | ......... | A01N 63/38 |
| | | | | 435/177 |
| 2018/0070586 A1 | 3/2018 | Kim | | |

FOREIGN PATENT DOCUMENTS

| | | | |
|---|---|---|---|
| CN | 101717301 A | 6/2010 | |
| CN | 104430307 A | 3/2015 | |
| CN | 109097056 A | 12/2018 | |
| EP | 0320483 A2 | 6/1989 | |
| JP | 2013172745 A | 9/2013 | |
| WO | 9806267 A1 | 2/1998 | |
| WO | 2014016302 A1 | 1/2014 | |
| WO | 2014041112 A1 | 3/2014 | |
| WO | 2014187963 A1 | 11/2014 | |
| WO | 2015136023 A1 | 9/2015 | |
| WO | 2017087939 A1 | 5/2017 | |
| WO | WO-2017087939 A1 * | 5/2017 | ............ A01N 25/10 |
| WO | 2018234996 A1 | 12/2018 | |

OTHER PUBLICATIONS

Liu, C. H., Wu, J. Y., & Chang, J. S. (2008). Diffusion characteristics and controlled release of bacterial fertilizers from modified calcium alginate capsules. Bioresource technology, 99(6), 1904-1910 (Year: 2008).*
Etminani, F., & Harighi, B. (2018). Isolation and identification of endophytic bacteria with plant growth promoting activity and biocontrol potential from wild pistachio trees. The plant pathology journal, 34(3), 208. (Year: 218).*
Bashan et al., (2002) Alginate microbeads as inoculant carriers for plant growth-promoting bacteria. Biol Fertil Soils 35: 359-368.
Cruz et al., (2013) Biological deterioration of alginate beads containing immobilized microalgae and bacteria during tertiary wastewater treatment. Appl Microbiol Biotechnol 97(22): 9847-9858.
Damasceno et al., (2013) Rhizobia survival in seeds coated with polyvinyl alcohol (PVA) electrospun nanofibres. Can J Microbiol 59(11): 716-719.
Haffner et al., (2016) Core-shell alginate@silica microparticles encapsulating probiotics. J Mater Chem B; Accepted Manuscript. DOI: 10.1039/C6TB02802K. 8 pages. Published in final version as: J Mater Chem B 4: 7929-7935.
Liu et al., (2008) Diffusion characteristics and controlled release of bacterial fertilizers from modified calcium alginate capsules. Bioresour Technol 99(6): 1904-1910.
Mortimer et al., (2016) Microbial Interactions with Nanostructures and their Importance for the Development of Electrospun Nanofibrous Materials used in Regenerative Medicine and Filtration. J Microb Biochem Technol 8(3): 195-201.
Przyklenk et al., (2017) A bioencapsulation and drying method increases shelf life and efficacy of Metarhizium brunneum conidia. Journal of Microencapsulation, DOI: 10.1080/02652048.2017. 1354941. Accepted manuscript; 36 pages.
Wen et al., (2017) Encapsulation of Bioactive Compound in Electrospun Fibers and Its Potential Application. J Agric Food Chem 65(42): 9161-9179.

* cited by examiner

*Primary Examiner* — Louise W Humphrey
*Assistant Examiner* — Trevor L Kane
(74) *Attorney, Agent, or Firm* — Raphael Bellum PLLC (57) ABSTRACT

A dehydrated composition containing a particle encapsulating one or more microorganisms is provided. The composition is useful for controlling the release of the microorganisms following rehydration and propagation within the particle.

21 Claims, 7 Drawing Sheets

ENCAPSULATED MICROORGANISMS AND METHODS OF USING SAME

FIELD OF THE INVENTION

The present invention relates to particles capable of releasing viable microorganisms encapsulated therein following a preset incubation and propagation period.

BACKGROUND OF THE INVENTION

Microorganisms are increasingly being used in agricultural, environmental and medical applications. In agriculture, microorganisms can be applied to plants or soil in order to increase crop productivity, protect plants from diseases and maintain soil viability.

When utilized in open settings (e.g., agriculture, environmental protection), microbial cells can be diluted, dispersed and inactivated/killed by the environment before providing the desired effect. To overcome this problem, higher starter doses of microbial cells are utilized requiring culturing to excess in advance of use.

Approaches for packaging of microbial cells for transport/delivery have been described and typically involve desiccation of microbial cells in order to maintain stability and sterility of the microbial product until activation. Dried microbial cells can be rehydrated at the target environment to reestablish the desired activity. However, drying can result in death of most of the packaged microbial cells.

U.S. Pat. No. 7,422,737 discloses cellular solid carriers comprising viable microorganisms capable of controlling plant pathogens. The cellular solid carriers are formed from water-soluble hydrocolloid beads dried under conditions which preserve their porosity, thereby allowing efficient release of microorganisms or diffusion of products derived from the microorganisms from the beads to the surrounding environment.

Przyklenk et al. (Journal of Microencapsulation, DOI: 10.1080/02652048.2017.1354941 (2017)) discloses the development of encapsulated and dried entomopathogenic fungus *Metarhiuzm brunneum* with reduced conidia content, increased conidiation, a high drying survival and enhanced shelf life. Dried beads were prepared with corn starch, potato starch, carboxymethylcellulose or autoclaved baker's yeast as fillers.

There is thus a need for, and it would be highly advantageous to have, a composition that encapsulates microorganisms and enables their propagation and timely release at a target environment such as a crop field or greenhouse.

SUMMARY OF THE INVENTION

The present invention is conducive to the propagation and release of microorganisms at a target environment in a manner that enhances their ability to survive in that environment. The present invention thus provides a composition that includes encapsulated microorganism(s) which can be propagated and released at a target environment in a controlled manner. The composition comprises a particle (e.g. a microparticle) encapsulating one or more viable microorganisms, wherein the particle comprises an inner core (lumen) containing the one or more microorganisms, optionally together with the nutrients required for their propagation, the inner core being surrounded by an outer shell layer which delays the dispersal of microorganisms from within the particle to the environment. The particle is dried and optionally stored before its application to the environment of choice. The outer shell layer is permeable to water but does not enable the release of microorganisms encapsulated therein for a predetermined period of time after rehydration. Hence, the microorganisms are maintained or retained within the particles until they have multiplied and can be released successfully to the environment in which they are required with greater chances of survival. The composition of the present invention thus provides the release of viable microorganisms in culture density or cell count suitable for uses such as increasing crop productivity, protecting plants from diseases and maintaining soil viability, even when the culture density or cell count prior to rehydration is low.

According to one aspect of the present invention, there is provided a dehydrated composition comprising a particle encapsulating one or more microorganisms, wherein the particle is composed of an inner core comprising the one or more microorganisms surrounded by an outer shell layer, wherein said outer shell layer is selectively permeable to a rehydrating fluid, and wherein upon fluid absorption, said outer shell layer degrades at a predetermined rate thereby releasing a plurality of microorganisms to the surrounding environment in a controlled manner, wherein the encapsulated microorganisms are present in the dehydrated composition at an initial concentration of less than about $1 \times 10^5$ colony forming units (CFU), and wherein following fluid absorption, the concentration of the encapsulated microorganisms is increased by at least 10-fold before the microorganisms are released to the surrounding environment. In certain embodiments, the dehydrated composition comprises a plurality of particles.

In various embodiments, the outer shell layer is designed to degrade gradually upon fluid absorption. In other embodiments, the outer shell layer is designed to be digested by the microorganisms contained therein. In further embodiments, the outer shell layer is sensitive to pH. In yet further embodiments, the outer shell layer is light-sensitive. In additional embodiments, the outer shell layer is sensitive to temperature changes. In other embodiments, the outer shell layer is sensitive to changes initiated by the propagation of the microorganisms thereby releasing the microorganisms in a controlled manner.

In some embodiments, the outer shell layer comprises a naturally occurring polymer, a synthetic polymer, or a semi-synthetic polymer, with each possibility representing a separate embodiment. In various embodiments, the outer shell layer comprises a water-degradable polymer. In certain embodiments, the polymer is selected from the group consisting of polyvinyl alcohol (PVA), polyvinylpyrrolidone (PVP), polyethylene oxide (PEO), polyethylene glycol (PEG), polycaprolacetone (PCL), polyurethane (PU), polyglycolic acid (PGA), polylactic acid (PLA), polylactic-co-glycolic acid (PLGA), poly-L-lactic acid (PLLA), cellulose derivatives, chitosan, chitin, hyaluronan (HA), gelatin, nylon 6, polyacrylonitrile (PAN), polylactide/polyhydroxybutyrate (PLA/PHB), alginate polymer, and a mixture or combination thereof. Each possibility represents a separate embodiment. In one embodiment, the polymer is PVA. In another embodiment, the polymer is gelatin. In yet another embodiment, the polymer is an alginate polymer.

In certain embodiments, the outer shell layer is formed from a polymer or polymer precursor configured to undergo a phase transition in response to a stimulus. In certain embodiments, the stimulus is chemically-induced. In other embodiments, the stimulus is physically-induced. In particular embodiments, the stimulus comprises a change in at least one of temperature, pH, light, and electric field, with each possibility representing a separate embodiment.

According to various embodiments, the composition is dehydrated to a water content of about 0.5% to about 10% by weight of the total weight of the composition, including each value within the specified range. It is contemplated that the outer shell layer of the particle is selectively permeable to a rehydrating fluid whereby upon rehydration (i.e. fluid absorption), propagation of the microorganism(s) within the particle is afforded followed by partial or complete degradation of the outer shell layer of the particle to provide the controlled release of the microorganisms encapsulated therein.

According to embodiments of the present invention, the particle has an average size ranging from about 1 to about 9,999 microns in diameter, including each value within the specified range. In some embodiments, the particle has an average size ranging from about 1 to about 100 microns in diameter, including each value within the specified range. In certain embodiments, the particle is at least 50 microns in diameter, for example about 50 to about 100 microns in diameter, including each value within the specified range. In additional embodiments, the average size of the particle is less than 100 microns in diameter.

According to other embodiments of the present invention, the particle encapsulates microorganisms at an initial concentration of less than about $1\times10^5$ colony forming units (CFU), for example about 1 to about $1\times10^5$ CFU, including each value within the specified range. In further embodiments, the particle encapsulates microorganisms at an initial concentration of less than about $1\times10^4$ CFU, for example about 1 to about $1\times10^4$ CFU, including each value within the specified range. In exemplary embodiments, the particle encapsulates microorganisms at an initial concentration of less than about $1\times10^3$ CFU, for example about 1 to about $1\times10^3$ CFU, including each value within the specified range. In yet other embodiments, the particle encapsulates microorganisms at an initial concentration of about 10 to about 1,000 CFU, including each value within the specified range.

It is contemplated that, upon rehydration, microincubation and propagation of the microorganism occurs, thereby resulting in a significant increase in the number of encapsulated microorganisms. In one embodiment, upon rehydration (fluid absorption), the concentration of the encapsulated microorganisms is increased by at least 2, 3, 4, 5, 6, 7, 8, 9, or even 10-fold as compared to naked non-encapsulated microorganisms. In certain embodiments, upon rehydration, the concentration of the encapsulated microorganisms is increased by at least 10-fold before the microorganisms are released to the surrounding environment. In another embodiment, upon rehydration, the concentration of the encapsulated microorganisms is increased by at least 20-fold before the microorganisms are released to the surrounding environment. In yet other embodiments, upon rehydration, the concentration of the encapsulated microorganisms is increased by at least 30-fold before the microorganisms are released to the surrounding environment. In further embodiments, the concentration of the encapsulated microorganisms is increased by at least 10-fold 24 hours following fluid absorption.

According to embodiments of the present invention, the microorganisms are released from the particle after a preset period. In one embodiment, a partial or complete degradation of the outer shell layer of the particle is designed to afford the release of the microorganisms initiating from about 24 hours to about 7 days following rehydration, including each value within the specified range. In certain embodiments, the outer shell layer of the particle is designed to have a degradation rate that affords the release of the microorganisms initiating from about 24 to about 96 hours following rehydration, including each value within the specified range. In other embodiments, the outer shell layer of the particle is designed to have a degradation rate that affords the release of the microorganisms initiating from about 24 to about 72 hours following rehydration, including each value within the specified range. In further embodiments, the release of the microorganisms is immediate after a preset period, i.e. a delayed release. In additional embodiments, the release of the microorganisms is modified by the presence of a sustained release agent within the inner core, thereby providing prolonged release of the microorganisms after a predetermined lag time. In accordance with these embodiments, the sustained release agent comprises a polymer which may be the same or different from the polymer forming the outer shell layer, with each possibility representing a separate embodiment.

According to further embodiments of the present invention, the inner core may further comprise one or more nutrients to support the growth of the encapsulated microorganism. In some embodiments, the nutrients include a carbon source, a nitrogen source, a phosphorous source, or a mixture or combination thereof, with each possibility representing a separate embodiment.

According to certain embodiments of the present invention, the outer shell layer may further be coated with at least one other coating layer. It is contemplated that the outer shell layer may further be coated with a plurality of layers, each having a different functionality. For example, the coating layer may exert different permeability than the outer shell layer thereby further modifying the release of the encapsulated microorganisms. In another example, the coating layer may be an adhesive coating layer thereby enabling the adhesion of the particle to a plant tissue (e.g. a plant seed).

According to another aspect of the present invention, there is provided a plant tissue coated with or in the vicinity of the particle described herein. Each possibility represents a separate embodiment. In one embodiment, the plant tissue is a plant seed.

According to yet another aspect of the present invention, there is provided a method of preparing a dehydrated composition comprising a particle as described herein, the method comprising: suspending one or more microorganisms in a solution optionally comprising one or more nutrients; encapsulating the one or more microorganisms and optional nutrients in a polymer thereby obtaining a particle composed of an inner core comprising said one or more microorganisms and optional nutrients surrounded by an outer shell layer; and dehydrating the particle. In some embodiments, the step of encapsulating the one or more microorganisms and optional nutrients comprises adding a polymer or polymer precursor to the suspension comprising the one or more microorganisms and optional nutrients, and inducing phase transition to the polymer or polymer precursor thereby obtaining a particle composed of an inner core comprising said one or more microorganisms and optional nutrients surrounded by an outer shell layer. In various embodiments, the phase transition comprises polymerization of the polymer precursor. In other embodiments, the phase transition comprises cross-linking of the polymer. In additional embodiments, the phase transition is effected in response to a stimulus that may be chemically induced or physically induced, with each possibility representing a separate embodiment. In particular embodiments, the stimulus comprises a change in at least one of temperature, pH, light, and electric field, with each possibility representing a separate embodiment.

According to embodiments of the present invention, there is provided a method of delivering a plurality of microorganisms to a target environment comprising rehydrating a dehydrated composition comprising a particle as described herein with a suitable amount of fluid thereby allowing the propagation and subsequent release of a plurality of microorganisms from the particle in a controlled manner.

According to particular embodiments of the present invention, the fluid is water.

Target environments include, but are not limited to, soil, phyllosphere, rhizosphere, sewage reclamation, toxic spill, fermentation, and the gastrointestinal tract. Each possibility represents a separate embodiment. In some embodiments of the present invention, the target environment is a soil environment.

In certain embodiments of the present invention, the microorganisms comprise endophytic bacteria.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION OF THE INVENTION

The present invention provides a composition that includes encapsulated microorganism(s) which can be propagated and released at a target environment in a controlled manner.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Approaches for preparing and storing microorganisms are well known in the art. While such approaches may be adequate for maintaining microorganisms viable until use, they are not suitable when the microorganisms are used in open settings (e.g., agriculture, environmental protection, etc.) since such conditions can dilute, disperse and inactivate the microorganisms before providing the desired effect. Accordingly, open settings typically require the application of very high concentrations of microorganisms such that following their dilution, dispersion and inactivation, there remains a sufficient amount of microorganisms that can exert their beneficial effects. However, it is not commercially feasible to use very high concentrations of microorganisms. The present invention provides a surprisingly advantageous composition that enables prolongation of shelf-life and lowering the viability threshold of microorganisms, thus being particularly suitable for use in open settings.

According to certain aspects and embodiments, there is provided a composition that can:

(i) maintain agriculturally/environmentally important microorganisms viable for extended period of time (months to years);

(ii) enable dispersal and release of a plurality of microorganisms in an environment such as a field in a controlled manner; and (iii) time the release of the plurality of microorganisms to the environment following a period in which the microorganisms propagate to a predetermined culture density while not being exposed to the environment.

The present invention affords the propagation of microorganisms within the confinement of protecting capsules until they reach a high enough concentration that enables their successful release to a target environment. This enables a reduction in the minimum initial dose of microorganisms to less than $1 \times 10^5$ colony forming units (CFU).

As is described hereinunder and in the Examples section which follows, there is provided a composition that includes one or more microorganism cells encapsulated within a particle. The particle is characterized by an inner core (lumen) surrounded by an outer shell layer which enables the selective inflow of a fluid into the particle to result in the propagation of the microorganism(s) within the particle lumen while preventing outflow of microorganisms until propagation results in a desired culture density or cell count. The particle therefore performs as a microincubator to microorganisms which can be applied to plants or soil for various uses including, but not limited to, increasing crop productivity, protecting plants from diseases, and maintaining soil viability.

As used herein and in the appended claims, the term "particle" refers to any sub-centimeter scale particle (e.g. about 1 to about 9,999 microns in size as measured along a selected axis, e.g. diameter). Typical dimensions for a particle can be up to 10,000 microns in outer diameter (OD) and up to 9,990 microns in lumen diameter (LD). In some embodiments, the particle has an average size ranging from about 1 to about 100 microns in diameter, including each value within the specified range, for example about 1, about 5, about 10, about 15, about 20, about 25, about 30, about 35, about 40, about 45, about 50, about 55, about 60, about 65, about 70, about 75, about 80, about 85, about 90, about 95, or about 100 microns. Each possibility represents a separate embodiment. In certain embodiments, the particle is at least 50 microns in diameter. In other embodiments, the particle is less than 100 microns in diameter. In further embodiments, the particle has an average size of about 50 to about 100 microns in diameter, including each value within the specified range. According to the principles provided herein, the particle may have any shape suitable for encapsulation of a microorganism within a lumen thereof. Exemplary shapes include, but are not limited to, spherical, oval, cylindrical, cube, and the like. Each possibility represents a separate embodiment. More complex shapes such as star, filament or sheet are also contemplated herein and may be advantageous for use in certain environments as is further detailed hereinunder.

Examples of microorganisms that can be encapsulated and cultured within the particle include, but are not limited to, bacteria, archaea, fungi (including yeast), protists and other prokaryotic and eukaryotic microorganisms. Each possibility represents a separate embodiment. One or more types of prokaryotic and/or eukaryotic microorganisms or species (e.g. 1, 2, 3 or more species of bacteria) can be encapsulated within a single particle. It is to be understood that the method and particle can be applicable to any microorganism. Non-limiting examples of microorganisms include:

Bacteria (Phylum Actinobacteria)—*Arthrobacter agilis, Arthrobacter aurescens, Arthrobacter globiformis, Arthrobacter nitroguajacolicus, Curtobacterium flaccumfaciens, Curtobacterium* sp., *Kocuria palustris, Microbacterium arborescens, Microbacterium oxydans, Paenarthrobacter nicotinovorans, Streptomyces lydius*, and *Streptomyces fulvissimus*. Each possibility represents a separate embodiment.

Bacteria (Phylum Bacteroidetes)—*Chryseobacterium lathyri, Flavobacterium endphyticum*, and *Flavobacterium johnsoniae*. Each possibility represents a separate embodiment.

Bacteria (Phylum Firmicutes)—*Bacillus amyloliquefaciens, Bacillus aquimaris, Bacillus endophyticus, Bacillus lehensis, Bacillus megaterium, Bacillus simplex, Paenibacillus* sp., *Bacillus subtilis, Bacillus toyonensis, Enterococcus casseliflavus*, and *Enterococcus faecalis*. Each possibility represents a separate embodiment.

Bacteria (Order Alphaproteobacteria)—*Rhizobium alamii, Rhizobium* sp., *Rhizobium leguminosarum, Rhizobium radiobacter, Rhizobium tropici, Shinella* sp., *Sinorhizobium meliloti, Sphingobium herbicidovorans, Ochrobactrum anthropi, Sphingobium yanoikuyae, Sphingomonas hankookensis, Sphingomonas koreensis, Sphingomonas pseudosanguinis*, and *Sphingomonas sanguinis*. Each possibility represents a separate embodiment.

Bacteria (Order Betaproteobacteria)—*Acinetobacter calcoaceticus, Acinetobacter* sp., *Enterobacter cloacae, Erwinia billingiae, Erwinia gerundensis, Lysobacter capsica*, and *Pantoea vagans*. Each possibility represents a separate embodiment.

Bacteria (Order Gammaproteobacteria)—*Acinetobacter calcoaceticus, Acinetobacter* sp., *Enterobacter cloacae, Erwinia billingiae, Erwinia gerundensis, Lysobacter capsica, Pantoea vagans, Pseudacidovorax intermedius, Pseudomonas alcaligenes, Pseudomonas benzenivorans, Pseudomonas borborid, Pseudomonas chlororaphis, Pseudomonas extremaustralis, Pseudomonas fluorescens, Pseudomonas frederiksbergensis, Pseudomonas monteilii, Pseudomonas moraviensis, Pseudomonas plecoglossicida, Pseudomonas putida, Pseudomonas rizosphaerae, Pseudomonas sihuiensis, Pseudomonas stutzeri, Pseudomonas taiwanensis, Pseudomonas aeruginosa, Pseudoxanthomonas sacheonensis, Rosenbergiella* sp., *Serratia marcescens, Serratia nematodiphilia, Serratia plymuthica, Stenotrophomonas geniculate, Stenotrophomonas maltophilia, Stenotrophomonas pavanii*, and *Stenotrophomonas nitritireducens*. Each possibility represents a separate embodiment.

Archaea—*Pyrococcus furiosus, Metallosphera sedula, Thermococcus litoralis, Methanococcus jannaschii, Sulfolobus solfataricus, Methanobacterium thermoautotrophicum*, and *Aeropyrum pernix*. Each possibility represents a separate embodiment.

Fungi (including yeast)—*Trichoderma harzianum, Rhizophagus irregularis, Aspergillus awamori, Metarhizium anisopliae, Sarocladium spinificis, Saccharomyces cerevisiae, Debaryomyces hansenii, Yarrowia lipolytica, Kluyveromyces marxianus, Zygosaccharomyces rouxii, Pichia pastoris, Sarocladium implicatum*, and *Candida versatilis*. Each possibility represents a separate embodiment.

Protista—Protozoa, *Protophyta* (algae) and molds. Each possibility represents a separate embodiment.

Other eukaryotes—various cell lines of various organisms (insect, mammalia) including stem cells such as embryonic stem cells, and primary cells such as epithelial cells. Each possibility represents a separate embodiment.

Currently preferred microorganisms include endophytic bacteria, particularly of species that are useful for agricultural use.

According to certain embodiments, the composition is dehydrated. As used herein, the term "dehydrated" refers to a composition having a water content of about 0.5 to about 10% by weight of the total weight of the composition, including each value within the specified range. For example, the water content of the dehydrated composition may be about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, or about 10% by weight of the total weight of the composition. Each possibility represents a separate embodiment. Dehydration can be effected using conventional methods such as lyophilization, oven drying, and the like.

According to some embodiments, the dehydrated composition comprises a particle as described herein. According to other embodiments, the dehydrated composition comprises a plurality of particles as described herein. The particle is configured to enable the release of a plurality of microorganisms following rehydration of the composition and propagation of the microorganism(s) within the particle.

This enables the microorganism(s) to propagate within the particle to a density/cell count which ensures viability and function in the target environment to which it is released.

In order to support propagation of microorganisms, the particle can optionally include growth nutrient(s) that provide a source of carbon, nitrogen, phosphorous (phosphates), potassium, and microelements to the microorganisms (when in a fluid medium). The type and concentration of such nutrients (in the rehydrating fluid within the microparticle) can be determined by a person of ordinary skill in the art depending on the type of microorganism encapsulated. Within the scope of the present invention is a dehydrated composition comprising a plurality of particles, each particle encapsulates a different species of microorganism together with nutrients suitable for its propagation, the plurality of particles further surrounded by an outer shell layer as described herein for the controlled release of the different microorganisms from their respective particles in a controlled manner.

Examples of nutrients suitable for supporting propagation of microorganisms are provided in the Examples section which follows. Typically, the nutrients include carbohydrates (e.g. glucose, sucrose, molasses, cellulose, and starch), vitamins, and the like. Furthermore, suitable growth media such as, but not limited to, Nutrient Broth (NB), Luria Bertini (LB) broth, Bushnell-Haas Broth (BHB), Trypticase Soy Broth (TSB), and the like may be used. Each possibility represents a separate embodiment. In certain embodiments, the outer shell layer may be biodegradable such that it provides the nutritional support to the encapsulated microorganisms. A degradable particle can also provide some or all of the nutrients needed to support microorganism growth. For example, alginate, cellulose derivatives, carrageenan, gelatin, and pectin particles are made of proteins or polysaccharides that can be degraded to support the growth of the encapsulated microorganisms. In accordance with these embodiments, the outer shell layer partially or completely degrades due to digestion or consumption by the encapsulated microorganisms.

According to certain aspects and embodiments of the present invention, the dehydrated composition provides the encapsulation of one or more microorganism cells at an initial concentration of less than about $1\times10^5$ colony forming units (CFU). The term "initial concentration" as used herein refers to the concentration of viable microorganisms (single or multiple types or species) just before rehydration, i.e. at time zero before fluid absorption prior to incubation and propagation. It is contemplated that a concentration of microorganisms in freshly made capsules prior to storage may be higher than $1\times10^5$ CFU. However, during storage, the concentration of viable microorganisms is typically reduced such that the initial concentration at time zero before fluid absorption is less than about $1\times10^5$ CFU. According to the principles provided herein, due to loss of viability of cells during formulation and storage, the concentration of microorganisms encapsulated within the particle can be significantly lower than that required to be effective in a target environment. A relatively small number of surviving cells can grow back to occupy the lumen (interior) of the capsule using the provided nutrients and nutrients derived from the dead cells. Even when the cell count prior to rehydration is low, the particle of the present invention is designed to perform as a microincubator upon rehydration to afford the release of a plurality of microorganisms to the target environment only when the culture density or cell count reaches a certain predetermined value suitable for exerting the desired effect.

In some embodiments, the initial concentration of encapsulated microorganisms is about 1 to about $1\times10^5$ CFU, including each value within the specified range, for example about 1, about 10, about 20, about 30, about 40, about 50, about 60, about 70, about 80, about 90, about 100, about 150, about 200, about 250, about 300, about 350, about 400, about 450, about 500, about 550, about 600, about 650, about 700, about 750, about 800, about 850, about 900, about 950, about 1,000, about 1,500, about 2,000, about 2,500, about 3,000, about 3,500, about 4,000, about 4,500, about 5,000, about 5,500, about 6,000, about 6,500, about 7,000, about 7,500, about 8,000, about 8,500, about 9,000, about 9,500, about 10,000, about 15,000, about 20,000, about 25,000, about 30,000, about 35,000, about 40,000, about 45,000, about 50,000, about 55,000, about 60,000, about 65,000, about 70,000, about 75,000, about 80,000, about 85,000, about 90,000, about 95,000, or about 100,000 CFU. Each possibility represents a separate embodiment. In other embodiments, the initial concentration of encapsulated microorganisms is about 1 to about $1\times10^4$ CFU, including each value within the specified range, for example about 1, about 10, about 20, about 30, about 40, about 50, about 60, about 70, about 80, about 90, about 100, about 150, about 200, about 250, about 300, about 350, about 400, about 450, about 500, about 550, about 600, about 650, about 700, about 750, about 800, about 850, about 900, about 950, about 1,000, about 1,500, about 2,000, about 2,500, about 3,000, about 3,500, about 4,000, about 4,500, about 5,000, about 5,500, about 6,000, about 6,500, about 7,000, about 7,500, about 8,000, about 8,500, about 9,000, about 9,500, or about 10,000 CFU. Each possibility represents a separate embodiment. In yet other embodiments, the initial concentration of encapsulated microorganisms is about 10 to about 1,000 CFU, including each value within the specified range for example about 10, about 20, about 30, about 40, about 50, about 60, about 70, about 80, about 90, about 100, about 150, about 200, about 250, about 300, about 350, about 400, about 450, about 500, about 550, about 600, about 650, about 700, about 750, about 800, about 850, about 900, about 950, or about 1,000 CFU. Each possibility represents a separate embodiment.

Upon rehydration, the selective permeability of the outer shell layer results in a significant increase in the number of encapsulated microorganisms. As used herein, the term "selective permeability" or "selectively permeable" refers to a shell layer which affords fluid inflow upon rehydration while preventing the release of the microorganisms and/or nutrients from the particle for a predetermined period of time after rehydration during which microincubation and propagation of the microorganisms occur. In certain embodiments, microincubation and propagation of the microorganisms result in at least a 2, 3, 4, 5, 6, 7, 8, 9, or even 10-fold increase in the density or cell count of the microorganisms as compared to naked non-encapsulated microorganisms' density or cell count at a predetermined period of time after rehydration. In one embodiment, upon rehydration (fluid absorption), the concentration of the encapsulated microorganisms is increased by at least 10-fold before the microorganisms are released to the surrounding environment. In various embodiments, upon rehydration, the concentration of the encapsulated microorganisms is increased by at least 20-fold before the microorganisms are released to the surrounding environment. In certain embodiments, upon rehydration, the concentration of the encapsulated microorganisms is increased by at least 30-fold before the microorganisms are released to the surrounding environment.

Following microincubation and propagation, a partial or complete degradation or erosion of the outer shell layer of the particle occurs, thereby affording the delayed release of the encapsulated microorganisms. As used herein, the term "delayed release" refers to the initiation of release of the encapsulated microorganisms after a certain lag time following fluid absorption. Typically, the release of the encapsulated microorganisms is effected from about 24 hours to about 7 days following rehydration, including each value within the specified range. For example, the release of the encapsulated microorganisms may be effected about 24 hours, about 48 hours, about 72 hours, about 96 hours, about 120 hours, about 144 hours, or about 168 hours (7 days) following rehydration. Each possibility represents a separate embodiment. In certain embodiments, release of the encapsulated microorganisms is effected from about 24 to about 96 hours following rehydration, including each value within the specified range, for example, about 24, about 48, about 72, or about 96 hours following rehydration. Each possibility represents a separate embodiment. In some embodiments, the concentration of the encapsulated microorganisms is increased by at least 10-fold 24 hours following fluid absorption. In other embodiments, the concentration of the encapsulated microorganisms is increased by at least 10-fold 48 hours following fluid absorption. In yet other embodiments, the concentration of the encapsulated microorganisms is increased by at least 10-fold 72 hours following fluid absorption. In further embodiments, the concentration of the encapsulated microorganisms is increased by at least 10-fold 96 hours following fluid absorption. In some embodiments, the concentration of the encapsulated microorganisms is increased by at least 20-fold 24 hours following fluid absorption. In other embodiments, the concentration of the encapsulated microorganisms is increased by at least 20-fold 48 hours following fluid absorption. In yet other embodiments, the concentration of the encapsulated microorganisms is increased by at least 20-fold 72 hours following fluid absorption. In further embodiments, the concentration of the encapsulated microorganisms is increased by at least 20-fold 96 hours following fluid absorption. In some embodiments, the concentration of the encapsulated microorganisms is increased by at least 30-fold 24 hours following fluid absorption. In other embodiments, the concentration of the encapsulated microorganisms is increased by at least 30-fold 48 hours following fluid absorption. In yet other embodiments, the concentration of the encapsulated microorganisms is increased by at least 30-fold 72 hours following fluid absorption. In further embodiments, the concentration of the encapsulated microorganisms is increased by at least 30-fold 96 hours following fluid absorption.

According to certain aspects and embodiments, the outer shell layer of the particle is formed from a polymer or polymer precursor configured to undergo a phase transition in response to a stimulus. The stimulus may be chemically induced or physically induced with each possibility representing a separate embodiment. Non-limiting examples of stimulus include a change in at least one of temperature, pH, light, and electric field, with each possibility representing a separate embodiment. The phase transition may be reversible or irreversible with each possibility representing a separate embodiment. An exemplary phase transition comprises the polymerization of a polymer precursor. Another exemplary phase transition comprises the cross-linking of polymer chains.

Several approaches can be used to provide the particle as described herein. In one approach the particle can be fabricated from fluid-degradable material made of single polymers or a plurality of polymers at a desired mixing ratio, density and thickness to achieve the required properties such as permeability and erosion or degradation rate. Synthetic, semi-synthetic or natural polymers can be optionally blended with proteins for the purpose of improving the process and the mechanical properties of fibers forming the outer shell. Polymers utilized in this way include, but are not limited to, polyethylene oxide (PEO), polyvinyl alcohol (PVA), polyvinylpyrrolidone (PVP), polyethylene glycol (PEG), polycaprolacetone (PCL), polyurethane (PU), polyglycolic acid (PGA), polylactic acid (PLA), polylactic-co-glycolic acid (PLGA), poly-L-lactic acid (PLLA), cellulose derivatives, chitosan, chitin, and hyaluronan (HA), gelatin, alginate polymer, and a mixture or combination thereof. Each possibility represents a separate embodiment. In one embodiment, the polymer is other than carboxymethyl cellulose (CMC). The particle can be prepared e.g. using extrusion designed to afford an outer shell layer with selective permeability.

In certain embodiments, the outer shell layer comprises polyvinyl alcohol (PVA). PVA is known to be available at various degrees of polymerization (molecular weight) and/or hydrolysis. Within the scope of the present invention is a single grade PVA or a combination of PVAs of different grades. Each possibility represents a separate embodiment. Grades of PVA suitable as an outer shell layer according to embodiments of the present invention include, but are not limited to, hydrolyzed PVA having a degree of hydrolysis of at least about 10%, 20%, 30%, 40%, 50%, 60%, 70%, 80%, 90%, 95%, 96%, 97%, 98%, 99%, or even 100% (fully hydrolyzed). Each possibility represents a separate embodiment. In specific embodiments, the outer shell layer comprises hydrolyzed PVA having a degree of hydrolysis of about 87% to about 99%, including each value within the specified range. Within the scope of the present invention is PVA of different chain lengths including, but not limited to, PVA having a molecular weight ranging from about 1 to about 500 kilodaltons (KD), for example about 10 to about 250 KD, preferably about 25 to about 125 KD, including each value within the specified ranges. For example, the PVA may have a molecular weight of about 1, about 5, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, or about 500 kD. Each possibility represents a separate embodiment. In other embodiments, the outer shell layer comprises gelatin. The amount of polymer used for fabricating the particle can vary as is known in the art. Typically the amount of polymer in the outer shell layer ranges from about 0.01% to about 30% (w/v), for example about 0.1% to about 20% (w/v), or about 1% to about 20% (w/v), including each value within the specified ranges.

Alternatively or additionally, electrical current (electrospinning) can be used while performing extrusion on synthetic and natural biopolymers, such as nylon 6 and polyethylene oxide (PEO), polyacrylonitrile (PAN) and a composite of polylactide/polyhydroxybutyrate (PLA/PHB) (Wen et al. J. Agric. Food Chem. 65(42), 9161-9179, doi:

10.1021/acs.jafc.7b02956 (2017); Mortimer et al., J. Microb. Biochem. Technol. 8, 3; DOI: 10.4172/1948-5948.1000285 (2016)).

According to certain aspects and embodiments, the outer shell layer may be composed of fibrous polymer material, optionally comprising pores of different sizes. In accordance with these embodiments, the pores may be able to physically trap the encapsulated microorganisms and/or nutrients from being released to the environment while allowing sufficient fluid inflow during rehydration. In some embodiments, the average diameter of the pores ranges from about 1 micron to about 100 microns, including each value within the specified range, for example about 1, about 5, about 10, about 15, about 20, about 25, about 30, about 35, about 40, about 45, about 50, about 55, about 60, about 65, about 70, about 75, about 80, about 85, about 90, about 95, or about 100 microns. Each possibility represents a separate embodiment. In other embodiments, the average diameter of the pores ranges from about 20 microns to about 999 microns, including each value within the specified range.

According to some aspects and embodiments, the degradation or erosion of the outer shell layer may be triggered by changes in pH, light, temperature etc. Each possibility represents a separate embodiment. In additional embodiments, the degradation or erosion of the outer shell layer may be triggered by changes initiated by the propagation of the microorganisms thereby releasing the microorganisms in a controlled manner.

In various aspects and embodiments, the composition may further comprise a sustained release agent within the inner core thereby providing prolonged release of the microorganisms after a predetermined lag time. In accordance with these embodiments, following degradation of the outer shell layer, the composition serves as a reservoir of microorganisms which may be slowly released to the target environment. The sustained release agent typically comprises a polymer. Although the inner core and outer shell layer may comprise different polymers, embodiments in which the same polymer is used are also contemplated. It is to be understood that when using the same polymer in the inner core and outer shell layer, the physical properties of the inner core and outer shell layer may be distinct such that the outer shell layer is designed to degrade at a different rate than the inner core upon fluid absorption. Two or more fluid-degradable materials fabricating an inner core and outer shell layer having different degradation rates as described herein are contemplated by the scope of the present invention.

According to further embodiments of the present invention, the outer shell layer may be overcoated with at least one other coating layer or a plurality of coating layers, each having a different functionality such as, but not limited to, different permeability, different sensitivity to pH, light, temperature etc. In some embodiments, the layer overcoating the outer shell layer may be an adhesive coating layer thereby enabling the adhesion of the particle to a plant tissue (e.g. seeds).

According to certain aspects and embodiments, there is provided a method of preparing a dehydrated composition comprising a particle encapsulating one or more microorganisms for delivery of a plurality of microorganisms to a target environment comprising:
(i) suspending one or more microorganisms in a solution optionally comprising one or more nutrients;
(ii) encapsulating the one or more microorganisms and optional nutrients in a polymer thereby obtaining a particle composed of an inner core comprising said one or more microorganisms and optional nutrients surrounded by an outer shell layer; and
(iii) dehydrating the particle.

In some embodiments, step (ii) comprises adding a polymer or polymer precursor to the suspension comprising the one or more microorganisms and optional nutrients and inducing phase transition to the polymer or polymer precursor thereby obtaining a particle as described herein. The phase transition may include polymerization of the polymer precursor or cross-linking of the polymer. Each possibility represents a separate embodiment. The phase transition may be induced physically (e.g. via heating, or light, or electrical field), or chemically (e.g. addition of a cross-linking agent). Typically, the phase transition is induced by subjecting the polymer or polymer precursor to a stimulus, such as, but not limited to, a change in at least one of temperature, pH, light, and electric field. Each possibility represents a separate embodiment. In other embodiments, step (ii) comprises adding (e.g. injecting) the suspension comprising the one or more microorganisms and optional nutrients to a preformed particle.

According to embodiments of the present invention, there is provided a method of delivering a plurality of microorganisms to a target environment. Following application of the dehydrated composition to a target environment, the composition is hydrated with a suitable amount of fluid (e.g. water) thereby allowing the propagation and subsequent release of a plurality of microorganisms from the particle to the target environment in a controlled manner. Target environments include, but are not limited to, soil, phyllosphere, rhizosphere, sewage reclamation, toxic spill, fermentation, and the gastrointestinal tract. Each possibility represents a separate embodiment. A currently preferred target environment is a soil environment. In accordance with these embodiments, the composition comprising a plurality of particles can be used as is by spraying (e.g. foliar spraying)/dusting/pouring to the environment (e.g. soil and/or plants) or it can be used in the vicinity (e.g. as a coating, co-seeding etc.) of plant tissue such as seeds.

According to certain aspects and embodiments, seeds (e.g. of common crops such as soy, corn, wheat or canola) can be coated with the composition of the invention using seed dusting. In other embodiments, gluing the particles to seeds using an adhesive chemical can be done. Following coating, the seeds can be stored until use. Planting and watering the seeds will rehydrate the particles and lead to the propagation and release of the microorganisms as is described hereinabove.

When used to spray/dust crops (e.g. fruit, leaves etc.), the particles can include a coating for facilitating adhesion of the particles to the crop tissue (especially when the crop is watered). Such a coating can include, for example, carboxymethyl cellulose (CMC) as adhesive material suitable for spraying crops. Additionally or alternatively, particles can be electrically charged to adhere to crops electrostatically when dusting. In certain embodiments, particles can be shaped so as to facilitate adherence to plant tissue. For example, the outer surface of the particle can include protrusions (e.g., stalks, pyramids) that can interact with plant leaf trichomes to facilitate adherence. A shape that increases the surface area can also be used in order to increase electrostatic or other interactions with plant tissue.

Figure 1:
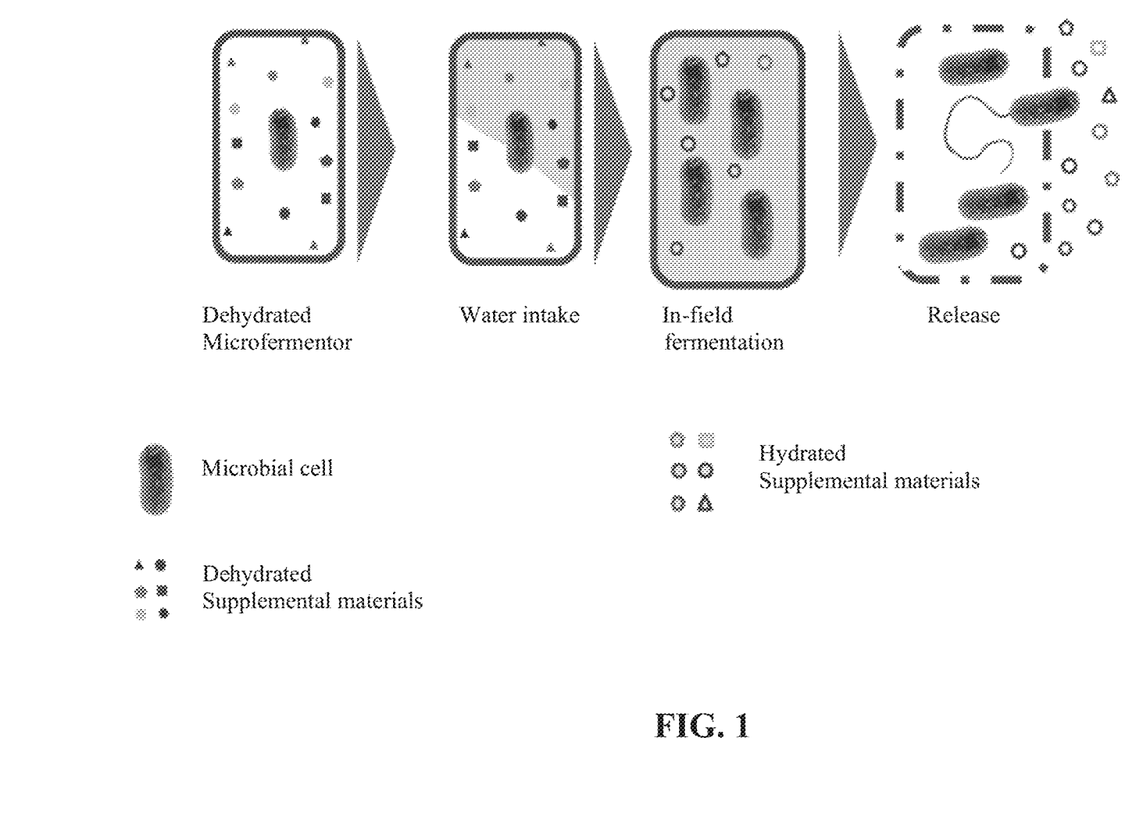
FIG. 1 schematically illustrates one or more cells of a microorganism and nutrients (supplemental materials) disposed within a dehydrated microparticle and the microincubation and controlled release of the encapsulated microorganisms following rehydration.
Figure 2:
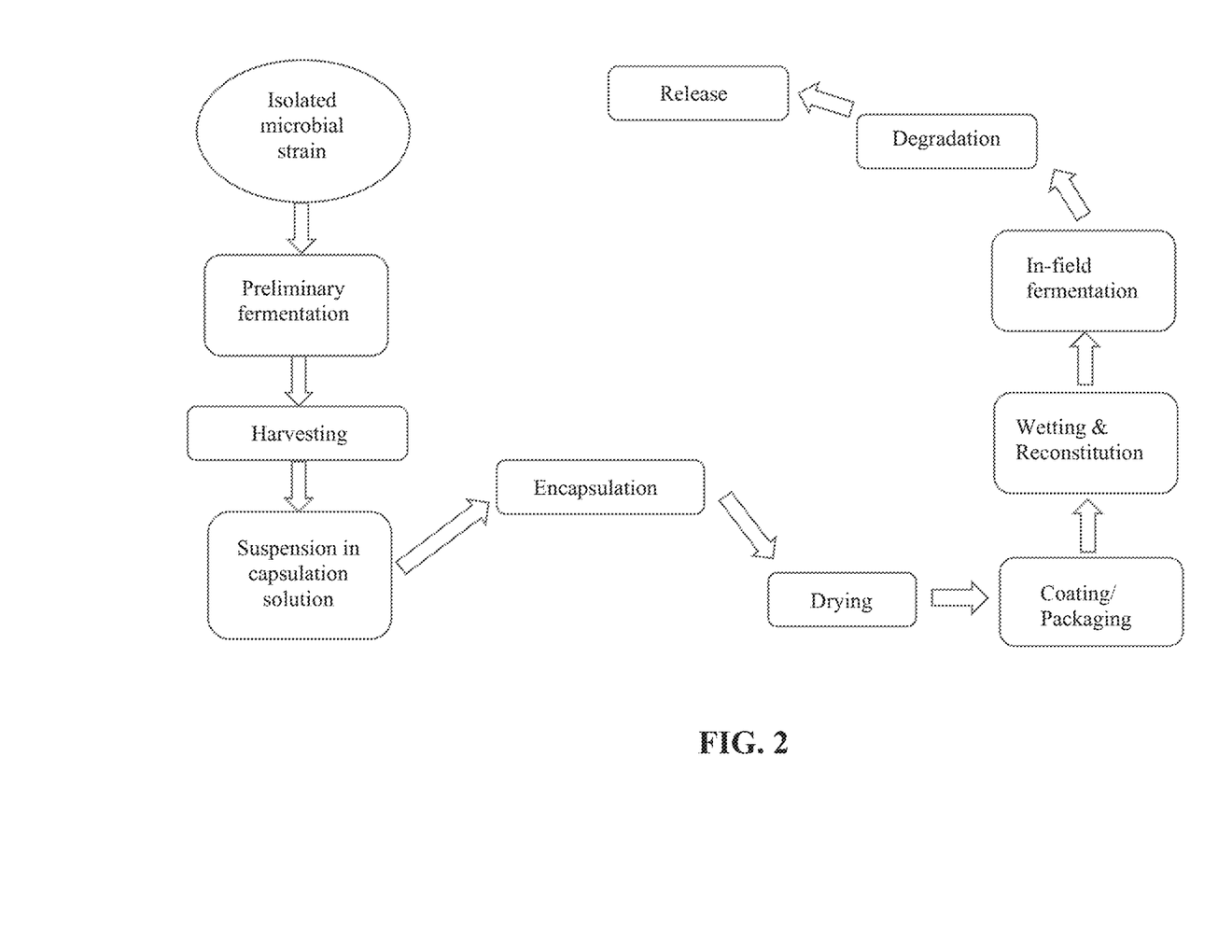
FIG. 2 schematically illustrates the steps of preparing one embodiment of the composition of the present invention.

Referring now to the drawings, FIG. 1 illustrates one embodiment of the present invention showing a composition containing one or more microorganisms (microbial cells) and nutrients (supplemental materials) within a lumen of a particle ('dehydrated microfermentor'). Following hydration ('water intake'), the nutrients form a medium suitable for propagation of the one or more microorganisms which then propagate ('in-field fermentation') within the particle until reaching a desired cell count/density before diffusing out to the target environment ('release'). The release is typically accompanied by outer shell layer degradation.

Preparation of various compositions of the present invention is described in detail in the Examples section that follows. Briefly, cells of the microorganism are suspended in solution, optionally further comprising nutrients that support propagation. The solution and cells are encapsulated within a particle (that is prefabricated or fabricated within the solution and cells) and the resulting composition is dehydrated.

FIG. 2 illustrates exemplary main steps of preparing particles within the scope of the present invention. The microorganism(s) is grown in a fermenter, then harvested and resuspended in a solution or suspension containing a polymer or a polymer precursor, as well as optional nutrients to support cell growth following rehydration. Polymerization or cross-linking is then induced physically and/or chemically as is known in the art, for example, using spinning and/or modified conditions such as pH, temperature, and/or the addition of a cross-linking agent (see Examples section), thereby encapsulating the microorganism(s) and optional nutrients. The suspension containing the encapsulated microorganism(s) and optional nutrients is then dehydrated to powder form, optionally followed by additional coating or packaging for storage and transport to a target environment. Upon application to a target environment, wetting (rehydration) and reconstitution is then effected to induce microfermentation, degradation and controlled release as illustrated in FIG. 1.

As used herein and in the appended claims, the term "about" refers to ±10%.

As used herein and in the appended claims, the singular forms "a", "an", and "the" include plural references unless the context clearly dictates otherwise. Thus, for example, reference to "a layer" includes a plurality of such layers and equivalents thereof known to those skilled in the art, and so forth. It should be noted that the term "and" or the term "or" are generally employed in its sense including "and/or" unless the context clearly dictates otherwise.

It will be apparent to one of ordinary skill in the relevant art that suitable modifications and adaptations to the compositions, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, methods, and processes described herein include all actual or potential combinations of embodiments, aspects, options, examples, and preferences herein described. The exemplary compositions described herein may omit any component, substitute any component disclosed herein, or include any component disclosed elsewhere herein. The ratios of the mass of any component of any of the compositions disclosed herein to the mass of any other component in the composition or to the total mass of the other components in the composition are hereby disclosed as if they were expressly disclosed. Furthermore, the foregoing discussion discloses and describes merely exemplary embodiments. Additional objects, advantages, and novel features of the present invention will become apparent to one ordinarily skilled in the art upon examination of the following examples, which are not intended to be limiting.

EXAMPLES

Reference is now made to the following examples, which together with the above descriptions, illustrate the invention in a non-limiting fashion.

Example 1: Fermentation of Bacterial Strains Prior to Encapsulation

One strain (*Pseudomonas chlororaphis*, Phylum Proteobacteria) was tested for microfermentation in soil. It is to be understood that other strains e.g. *Arthrobacter globiformis* (Phylum Actinobacteria) and *Bacillus endophyticus* (Phylum Firmicutes) can also be used. Strains are removed from cryogenic or lyophilized storage. Inocula are prepared by either direct transfer to a suitable liquid media (LB, NB, TSB, R2A or other bacteriological growth medium) and incubation in a shaker incubator for 10-15 hours at 200 rpm and 28° C., or transfer to an agar plate media (LB, NB, TSB, R2A or other bacteriological growth medium) and growth for 24-48 hours before selecting colonies for transfer to a suitable liquid media. The inocula are transferred to a shake flask or a fermenter. Fermenter includes standard pH and dissolved oxygen (DO) probes; temperature and pH control; and programmed nutrient feeding. Media containing a suitable carbon source such as glucose, sucrose, molasses, cellulose or starch; a nitrogen source such as peptones, or peptides; additional nutrients required by the organism such as minerals and vitamins; and antifoaming compounds, such as silicones or polypropylene glycol P2000, are sterilized in the fermenter or in an autoclave, and transferred aseptically to the sterile flask or fermenter to initiate growth. Before harvest after 12-48 hours, the flask or fermenter is sampled and evaluated for cell density. Growth is continued in the flask or fermenter until optical density (OD) at 600 nm is greater than 10, indicating that the colony forming units (CFUs) are greater than $1\times10^9$ CFUs/ml. The flask or fermenter contents are centrifuged at 10,000 g and 4° C. for 10 minutes, to recover the bacteria. From a fermenter, a bacterial paste of more than 30 g/liter is recovered. The sample is diluted 1:10 in phosphate buffered saline (PBS, pH 7.0) or other desired solution. A small sample (1 ml) is serially diluted 10-fold several times in sterile PBS. The resulting diluted bacterial suspensions are then plated on sterile LB, NB, TSB, R2A or other bacteriological culturing medium. After 48 hours of incubation at 28° C. in the dark, colony forming units (CFUs) in each dilution are enumerated. Calculation of CFUs per 1 ml is performed by multiplying CFUs in each dilution by the dilution factors and averaging the results obtained from the different dilutions.

Static fermentation can also be used, where the inocula is spread on agar media in bottles or plates. Growth is continued until obtaining relevant physiological stage, and the microorganism is collected by agar wash with phosphate buffered saline (PBS, pH 7.0) or other desired solution. A small sample (1 ml) is serially diluted 10-fold several times in sterile PBS for CFU assay as described above.

Example 2: Formulation with Chemical Additives Without Encapsulation

Three methods are employable as follows:

Method 1: Bacteria are harvested by centrifugation at 10,000 g and 4° C. for 10 min. The pellet is mixed with 20% MicroCel-E® synthetic calcium silicate or Sipernat® 225 synthetic amorphous silicon dioxide, 10% mannitol, maltodextrin, sorbitol, and/or skim milk powder using a coffee grinder. The wet powder is dried in a force air oven at 40° C.

Method 2: Bacteria are harvested and re-suspended in water to a tenth of the initial (fermentation) volume. The bacterial suspension is mixed with 5% mannitol, maltodextrin, sorbitol, and/or skim milk powder and is sprayed onto MicroCel-E® or Sipernat® 225 using a Strea-1 fluid bed dryer. Inlet temperature is kept at 40° C.

Method 3: Bacteria are harvested and re-suspended in water to a tenth of the initial (fermentation) volume. The bacterial suspension is mixed with 5% mannitol, maltodextrin, sorbitol, skim milk powder, and/or gum arabic or 3% skim milk powder and 2% gum arabic and is dried with a Buchi™ B-290 spray dryer. Inlet temperature is kept at 60° C.

Example 3: Encapsulation

Electrospinning

Generation of electrospun capsules is conducted in a manner known in the art, such as in Damasceno et al. (Can. J. Microbiol. 59, 716-719 (2013)). Bacteria are harvested by centrifugation at 10,000 g and 4° C. for 10 min and the paste is re-suspended in sterile 0.9% NaCl, containing glucose, sucrose, molasses, cellulose or starch, at a concentration of up to 100 µg/liter, and an extract or digest of casein, soy, corn and/or yeast at a concentration of 20-200 µg/liter. A sterilized solution of 30% PVA in distilled water is added to the suspended cells to a final concentration of 15% PVA. To polymerize the capsules around the microbial cells, the solution is transferred to 5 ml syringes, and extruded at a syringe descent rate of 0.01 mm/s through a needle at a voltage of 22 kV and into a collection tube at a distance of 14 cm, in a manner calculated to create capsules of 50 µm diameter, with a permeability of 0.5 kDa molecular weight cut-off (MWCO). The capsules are dried in the collection tubes for 2 hours.

Alginate Encapsulation

Method 1: Bacteria are harvested by centrifugation at 10,000 g and 4° C. for 10 min and the paste is resuspended in sterile 0.9% NaCl. 5% Skim milk powder, glucose, maltodextrin, NB and/or LB are added to the bacterial suspension prior to the mixing with the alginate solution. The suspension is adjusted to a cell concentration of ~1×10$^8$ CFU/ml. A 2% (w/v) low viscosity alginate solution is prepared in dH$_2$O and mixed 1:10 with the bacterial suspension. The suspension is then extruded through an 80 micron nozzle of a Buchi™ B-390 Encapsulator (Buchi™ GmbH, Flawil, Switzerland) into a beaker filled with 0.2 M CaCl$_2$ under fast agitation. Beads are hardened in CaCl$_2$ for 30 min, filtered off with a vacuum pump, rinsed with dH$_2$O, filtered again and dried by lyophilization.

Method 2: Bacteria are harvested by centrifugation at 10,000 g and 4° C. for 10 min and the paste is re-suspended in sterile 0.9% NaCl. The suspension is adjusted to a cell concentration of ~1×10$^8$ CFU/ml. 5% Skim milk powder or glucose, maltodextrin, NB and/or LB are added to the bacterial suspension prior to the mixing with the alginate solution. A 2% (w/v) low viscosity alginate solution is prepared in dH$_2$O and mixed 1:10 with the bacterial suspension. The mixture is added dropwise with the aid of a 10-ml sterile syringe into 0.2 M CaCl$_2$ that is gently stirred at room temperature. The beads are maintained in the solution at room temperature for an additional 1 hour to obtain regular solid beads. The CaCl$_2$ solution is then pumped out, and the beads are washed twice with tap water. The beads are strained and dried in a forced air oven at 30° C.

Drop Encapsulation

A solution of 20% PVA of different grades (W/V; polymer/DDW), and/or gelatin was prepared according to manufacturer's recommendations. Several modifications, such as use of growth media including NB or LB, were optionally made. The suspension was then sterilized. Bacterial suspension was prepared by re-suspension of bacteria in relevant buffer or growth media. The suspension was adjusted to cell concentrations of 1×10$^2$-1×10$^{10}$ CFU/ml. Drops of polymer suspension were plated on glass. After a few minutes of polymerization, the bacterial suspension was injected into the polymers in each drop. The drop capsules were dried in a forced air oven at 30° C. for 3-4 hours. The flat capsules containing bacteria were removed by knife from the glass for immediate use or storage.

Example 4: Cell Viability Assessment in Storage

Formulation powder (100 mg) is suspended in 1 ml phosphate buffered saline (pH 7.0; PBS) and is 10-fold serially diluted in sterile PBS. The resulting diluted bacterial suspensions are then plated on sterile LB, NB, TSB, R2A or other bacteriological culturing medium. After 48 hours of incubation at 28° C. in the dark (thereby allowing degradation of the capsules), colony forming units (CFUs) in each dilution are enumerated. Calculation of CFUs per 1 gram of formulation is performed by multiplying CFUs in each dilution by the dilution factors and averaging the results obtained from the different dilutions of each formulation powder.

Example 5: Cell Growth Assessment in Soil/On Seed

Formulation powder (100 mg) is mixed with 1 gram of soil in a sealed 15 ml tube. Then, 500 µl of tap water are added into the mixture and the tube is incubated for 5 days at 17° C. in the dark. Strain viability is assessed every 24 hours for 4 days. At each time point, sterile PBS is added to a tube to a final volume of 5 ml, the tube is vigorously mixed for 10 min and its contents are 10-folds serially diluted several times in sterile PBS. The resulting diluted bacterial suspensions are plated on sterile LB, NB, TSB, R2A or other bacteriological culturing medium. After 48 hours of incubation at 28° C. in the dark, colony forming units (CFUs) in each dilution are enumerated. Calculation of CFUs per 1 gram of formulation is performed by multiplying CFUs in each dilution by the dilution factors and averaging the results obtained from the different dilutions of each tube.

The encapsulation of the present invention is envisioned to afford increase in growth and viability in soil relative to naked non-encapsulated microorganisms as well as microorganisms encapsulated with hitherto known packaging methods.

Example 6: Cell Growth at Low and High Initial Concentrations in Soil

*Pseudomonas chlororaphis* bacteria (2 mg) encapsulated using the drop encapsulation method described hereinabove in Example 3 were mixed in 2 grams of soil in a sealed 50 ml tube. Then, 900 µl of tap water were added into the mixture and the tube was incubated for up to 6 days at 19° C. in the dark. Bacterial viability was assessed every 24 hours over 4 days. At each time point, sterile PBS was added to a tube to a final volume of 10 ml, the tube was vortexed for 30 s and its contents were serially diluted 10-fold several times in sterile PBS. The resulting diluted bacterial suspensions were plated on sterile R2A or other bacteriological culturing medium containing selective antibiotics. After 48 hours of incubation at 28° C. in the dark, colony forming units (CFUs) in each dilution were enumerated. Calculation of CFUs per 1 mg of encapsulated particle was performed by multiplying CFUs in each dilution by the dilution factors and averaging the results obtained from the different dilutions of each tube.

The initial concentration of the bacteria was assayed by taking 1 mg of encapsulated particles per 1 ml sterile PBS, incubated for 60 min at RT, then serially diluted and plated on sterile R2A or other bacteriological culturing medium containing selective antibiotics. After 48 hours of incubation at 28° C. in the dark, CFUs in each dilution were enumerated.

Figure 3A:
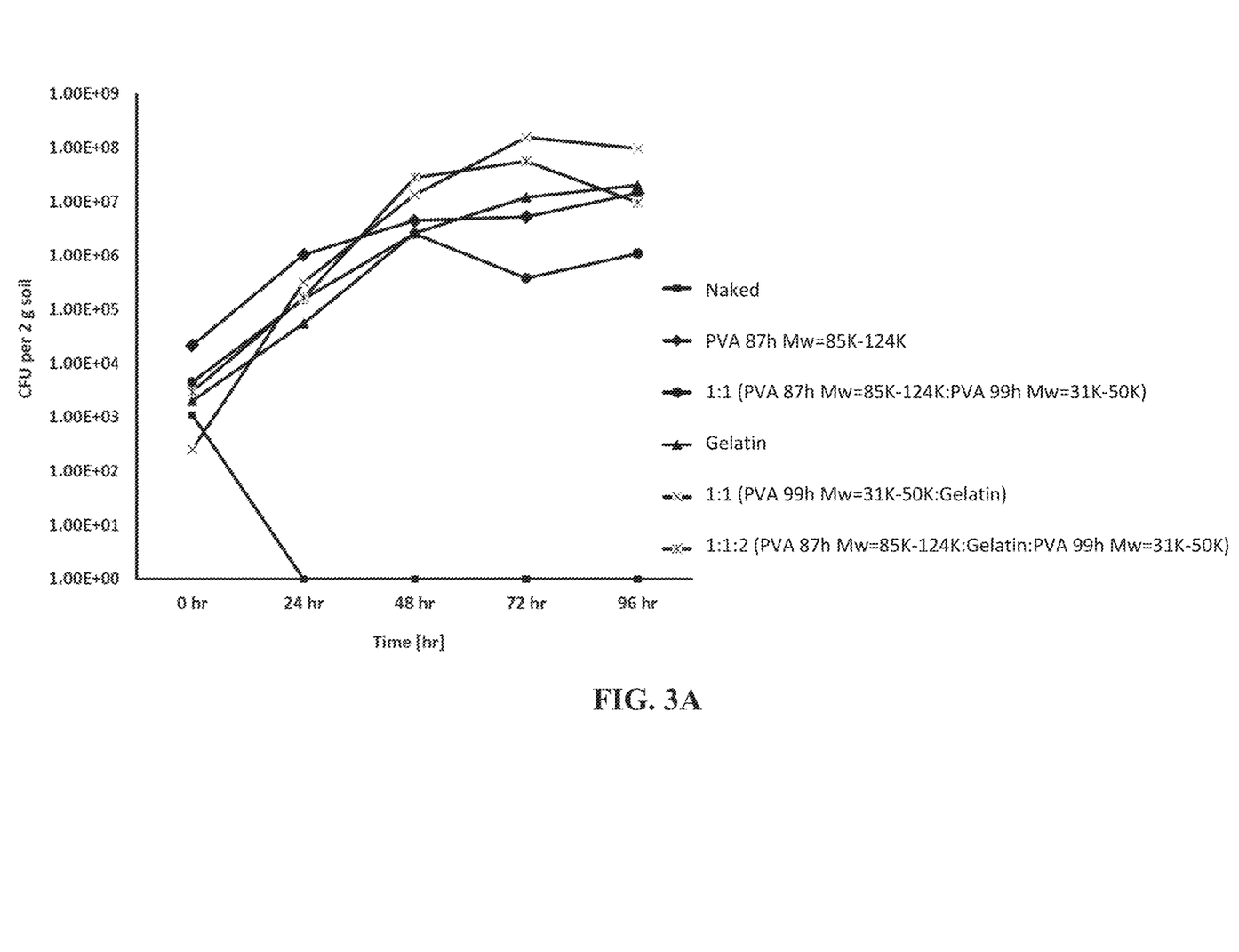
FIGS. 3A-3B show graphs of comparative results of propagation in soil of naked or encapsulated *Pseudomonas chlororaphis* in different polymers at initial concentrations of $10^2$-$10^5$ CFU per 2 grams of soil (FIG. 3A) and $10^5$-$10^6$ CFU per 2 grams of soil (FIG. 3B) over 96 hours.
Figure 3B:
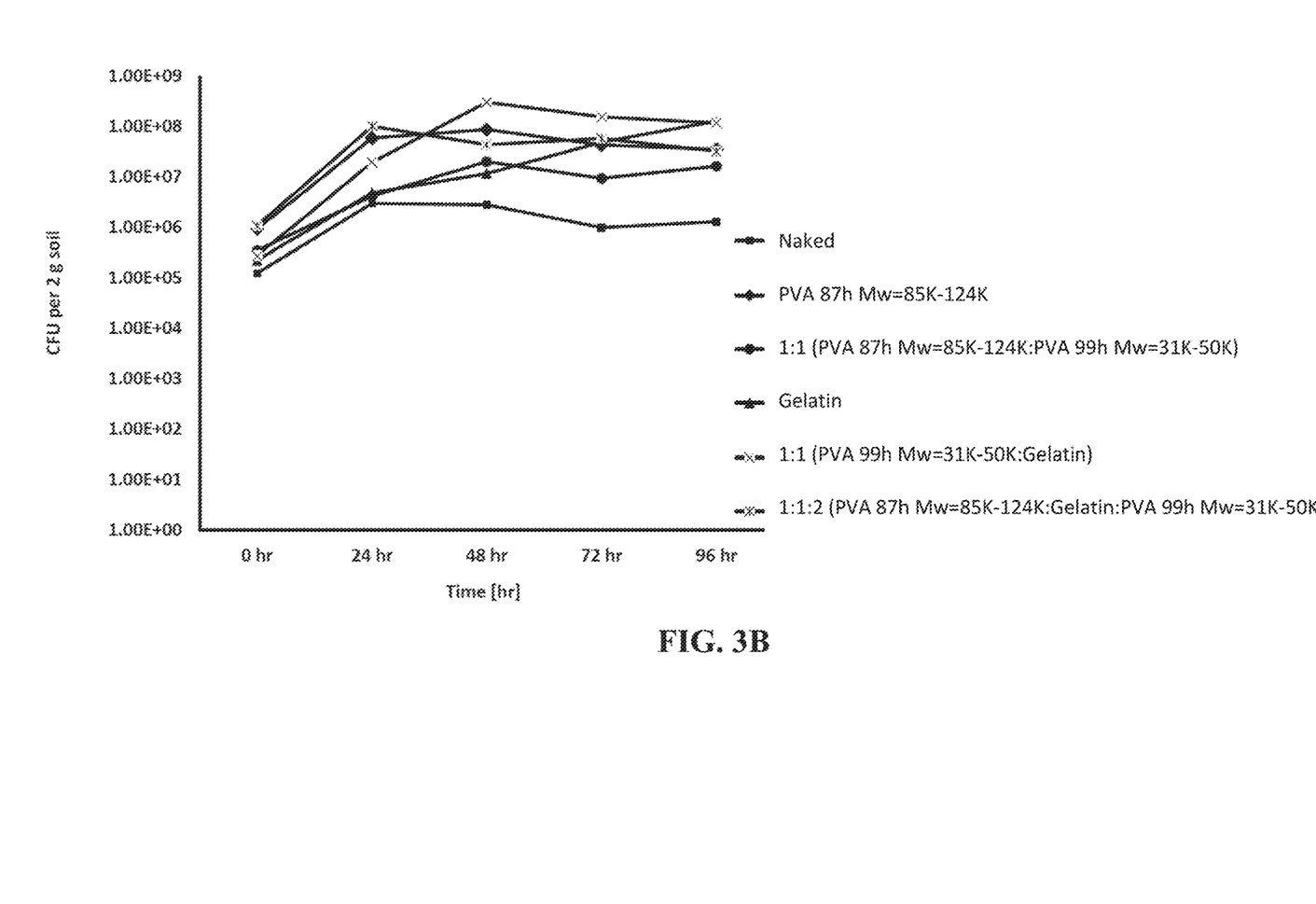

FIGS. 3A-3B show graphs which present comparative results of propagation in soil of naked (■) or encapsulated *Pseudomonas chlororaphis* in different polymers (♦ PVA 87 h Mw=85K-124K; ● 1:1 PVA 87 h Mw=85K-124K and PVA 99 h Mw=31K-50K; ▲ gelatin; ×1:1 PVA 99 h Mw=31K-50K and gelatin; and ✳ 1:1:2 PVA 87 h Mw=85K-124K, gelatin, and PVA 99 h Mw=31K-50K). FIG. 3A shows the propagation at initial concentrations of $10^2$-$10^5$ CFU per 2 grams of soil and FIG. 3B shows the propagation at initial concentrations of $10^5$-$10^6$ CFU per 2 grams of soil. Whereas at initial concentrations of $10^5$-$10^6$ CFU per 2 grams of soil both naked and encapsulated bacteria showed propagation, at initial concentrations of $10^2$-$10^5$ CFU per 2 grams of soil only the encapsulated bacteria showed propagation while the naked bacteria lost viability. These results demonstrate the advantage conferred by the encapsulation of the present invention at low initial concentrations.

Figure 4:
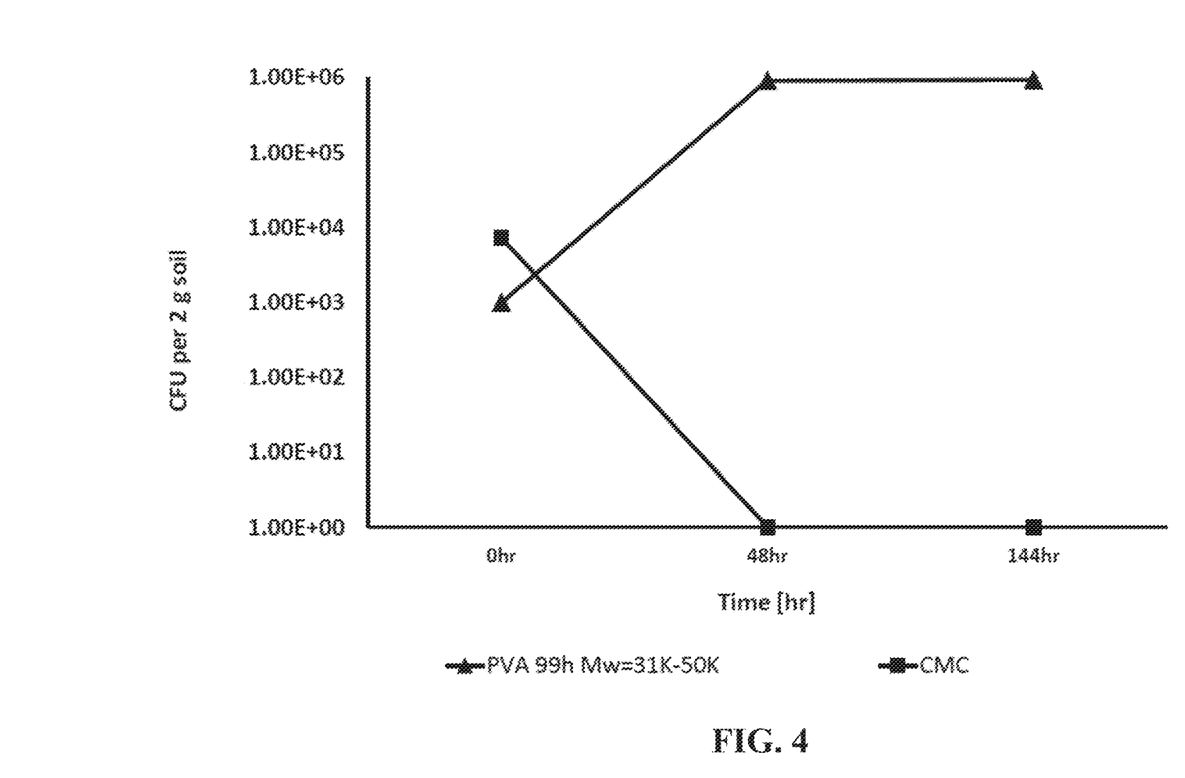
FIG. 4 shows a graph of comparative results of propagation in soil of *Pseudomonas chlororaphis* encapsulated in 10% PVA 99 h Mw=31K-50K and in 5% CMC over 144 hours.

FIG. 4 shows the comparative results of propagation in soil of *Pseudomonas chlororaphis* at initial concentrations of $10^3$-$10^4$ CFU per 2 grams of soil encapsulated in PVA 99 h Mw=31K-50K (▲) and in CMC (■) over 144 hours. Whereas the encapsulation in PVA showed bacterial propagation, the encapsulation in CMC yielded loss in viability, showing that not all types of encapsulation can provide bacterial propagation in the relevant environment. Without being bound by any theory or mechanism of action, it is contemplated that the CMC encapsulation did not afford proper propagation due to its higher solubility in water thereby resulting in the premature degradation of the capsule.

Example 7: Bacterial Growth Within a Polymer Capsule

*Pseudomonas chlororaphis* bacteria cells were encapsulated within the polymer using the drop encapsulation method as described hereinabove in Example 3. The dried capsules were then placed in the middle of R2A plates or any other nutrient plate and incubated at 28° C. for 24-72 hours. At time 0 and every 24 hours thereafter, 100 µl of DDW were pipetted on the edge of the plate, to provide water at diffusion rate. After 48 hours, the edges of the capsule were no longer smooth, suggesting the release of the bacteria.

Figure 5A:
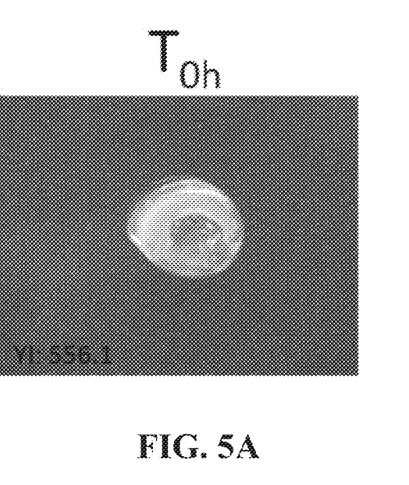
FIGS. 5A-5C illustrate the growth of *Pseudomonas chlororaphis* within a capsule, at time 0 (FIG. 5A), after 24 hours (FIG. 5B), and after 48 hours (FIG. 5C).
Figure 5B:
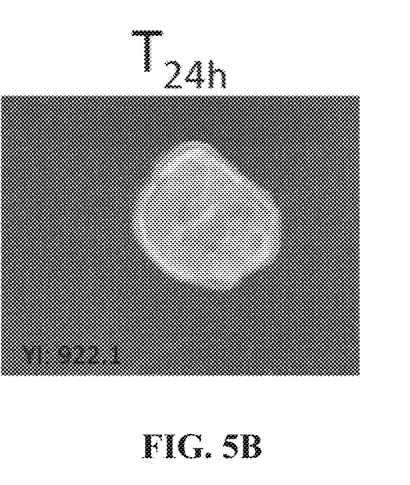
Figure 5C:
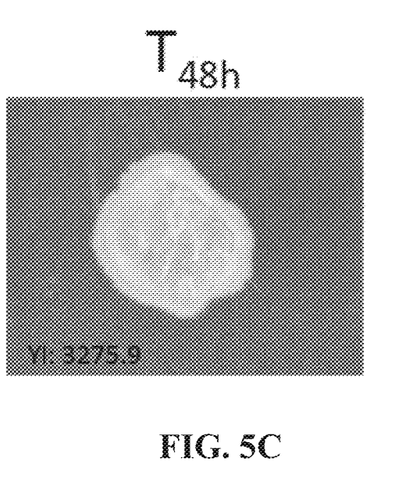

FIGS. 5A-5C illustrate the growth of *Pseudomonas chlororaphis* within the capsule, at time 0 ($T_{0h}$; FIG. 5A), after 24 hours ($T_{24h}$; FIG. 5B), and after 48 hours ($T_{48h}$; FIG. 5C). The light areas are the capsules, which expand with hydration. The rougher edges of the light area at 48 hours represent bacterial growth. Identity of growing bacteria was demonstrated by the development of color. Specifically, *Pseudomonas chlororaphis* at high bacterial dose develop a yellow to orange pigment color. At the indicated time points, the plates were photographed at high resolution in order to quantify the intensity of the developed color in the light areas. The color was quantified using the IMAGEJ software, as the intensity within the sampled area in the color hue range of 25-50 (representing yellow-orange pigmentation of *Pseudomonas chlororaphis*) multiplied by the percentage of colored area within the sampled area, and is shown on the bottom left corner of each figure. The intensity of the color at time 0 ($T_{0h}$), after 24 hours ($T_{24h}$), and after 48 hours ($T_{48h}$) was 556.1, 922.1, and 3275.9, respectively.

Example 8: Accelerated Model of Bacterial Release from a Polymer

In order to demonstrate release of the bacteria from the capsule, an accelerated model was used. The accelerated model affords the release from the capsule starting immediately after hydration and up to 70 minutes thereafter. It is contemplated that the release in soil is much slower, thereby enabling the bacteria to propagate within the capsule prior to release.

The accelerated model was prepared as follows: a modification of the drop encapsulation method described hereinabove in Example 3 was applied such that instead of preparing the drops on glass, the drops were prepared on the well corners of a 24 well plate and remained on the plate without removal. The bacteria used for this assay were GFP labeled. At time zero, 900 µl of DDW were added to each well and GFP emission was measured at 509 nm after excitation at 395 nm. Reads were recorded by 3 successive flashes at intervals of 5 min. Each data point represents an average of 4 independent repeats, with 3 flashes per repeat per time point.

Figure 6:
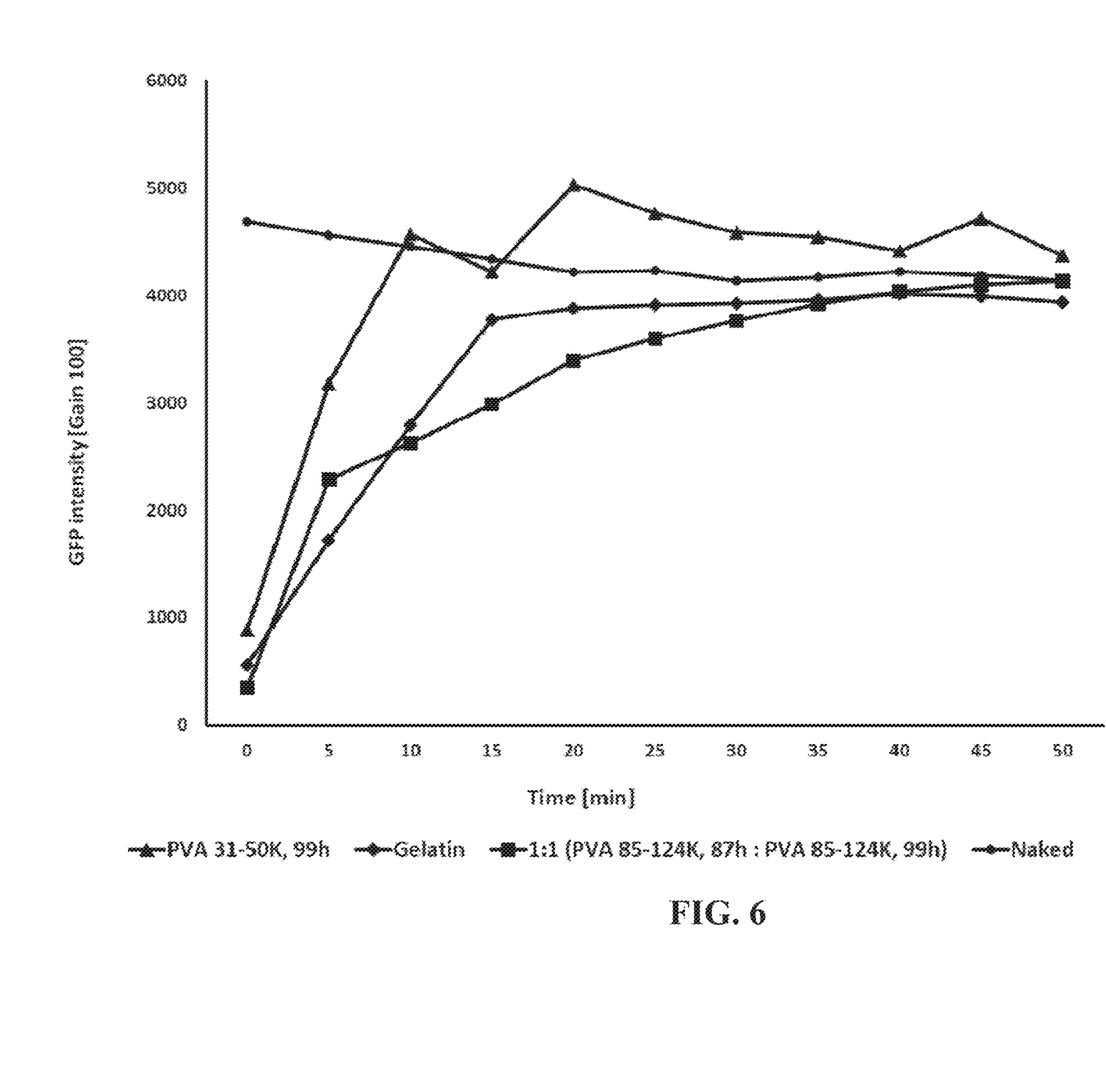
FIG. 6 shows a graph of comparative results of bacterial release from capsules in an accelerated model.

FIG. 6 shows graphs of bacterial release from various capsules (▲ PVA 31-50K, 99 h capsule; ♦ gelatin capsule; and ■ 1:1 PVA 85-124K, 87 h and PVA 85-124K, 99 h capsule) in the accelerated model. The results show the effective release of the bacteria from all capsules following rehydration. Naked bacteria used as control (●) showed constant GFP intensity.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A dehydrated composition comprising a delayed-release particle encapsulating one or more microorganisms, wherein the particle is composed of an inner core comprising the one or more microorganisms and one or more nutrients comprising at least one of a carbon source, a nitrogen source, and a phosphorous source, surrounded by an outer shell layer having a permeability of 0.5 kDa molecular weight cut-off (MWCO), thereby being selectively permeable to a rehydrating fluid while retaining the one or more microorganisms encapsulated within the particle, wherein the outer shell layer is configured to degrade upon fluid absorption, thereby releasing a plurality of encapsulated microorganisms to the surrounding environment in a delayed-release manner, wherein the encapsulated microorganisms are present in the dehydrated composition at an initial concentration of less than $1\times10^3$ colony forming units (CFU) per particle, and wherein following fluid absorption, the concentration of the encapsulated microorganisms is increased by at least 10-fold before the outer shell is degraded and the microorganisms are released to the surrounding environment.

2. The composition of claim 1, wherein the outer shell layer comprises a naturally occurring polymer, a synthetic polymer, or a semi-synthetic polymer; or wherein the outer shell layer comprises a water-degradable polymer; or wherein the outer shell layer comprises a polymer selected from the group consisting of polyvinyl alcohol (PVA), polyvinylpyrrolidone (PVP), polyethylene oxide (PEO), polyethylene glycol (PEG), polycaprolactone (PCL), polyurethane (PU), polyglycolic acid (PGA), polylactic acid (PLA), polylactic-co-glycolic acid (PLGA), poly-L-lactic acid (PLLA), cellulose derivatives, chitosan, chitin, hyaluronan (HA), gelatin, nylon 6, polyacrylonitrile (PAN), polylactide/polyhydroxybutyrate (PLA/PHB), alginate polymer, and a mixture or combination thereof.

3. The composition of claim 2, wherein the polymer is polyvinyl alcohol (PVA) or gelatin.

4. The composition of claim 1, wherein the outer shell layer is designed to be digested or consumed by the encapsulated microorganisms; or wherein the outer shell layer is formed from a polymer or polymer precursor configured to undergo a phase transition in response to a stimulus, wherein the stimulus comprises a change in at least one of temperature, pH, light, and electric field.

5. The composition of claim 1, wherein the particle is less than 100 microns in diameter.

6. The composition of claim 1, wherein the release of the microorganisms initiates about 24 to about 96 hours following fluid absorption; and/or wherein the concentration of the encapsulated microorganisms is increased by at least 10-fold about 24 hours following fluid absorption.

7. The composition of claim 1, wherein the microorganisms comprise endophytic bacteria.

8. The composition of claim 1 further comprising an adhesive coating layer over the outer shell layer.

9. The composition of claim 1, wherein the inner core further comprises a fluid-degradable material having a different degradation rate than the outer shell layer upon fluid absorption.

10. The composition of claim 1, comprising a plurality of particles.

11. The composition of claim 10, wherein the plurality of particles is further surrounded by an additional coating layer.

12. A plant tissue coated with or in the vicinity of the composition of claim 1.

13. The plant tissue of claim 12, being a plant seed.

14. A method of preparing a dehydrated composition comprising a particle encapsulating one or more microorganisms as claimed in claim 1, the method comprising:

(i) suspending one or more microorganisms in a solution comprising one or more nutrients;

(ii) encapsulating the one or more microorganisms and nutrients in a polymer, thereby obtaining a particle composed of an inner core comprising said one or more microorganisms and nutrients surrounded by an outer shell layer; and (iii) dehydrating the particle.

15. The method of claim 14, wherein step (ii) comprises adding a polymer or polymer precursor to the suspension comprising the one or more microorganisms and nutrients of step (i) and inducing phase transition to the polymer or polymer precursor, thereby obtaining a particle composed of an inner core comprising said one or more microorganisms and nutrients surrounded by an outer shell layer.

16. The method of claim 15, wherein the step of inducing phase transition to the polymer or polymer precursor comprises polymerization of the polymer precursor or cross-linking of the polymer; or wherein the step of inducing phase transition to the polymer or polymer precursor comprises subjecting the polymer or polymer precursor to a stimulus, wherein the stimulus comprises a change in at least one of temperature, pH, light, and electric field.

17. The method of claim 14, wherein step (iii) is performed to a water content of about 0.5% to about 10% by weight of the total dehydrated composition.

18. A method of delivering a plurality of microorganisms to a target environment, comprising rehydrating a dehydrated composition as claimed in claim 1 with a suitable amount of fluid, thereby allowing the propagation and subsequent release of a plurality of microorganisms from the particle to a target environment in a delayed-release manner.

19. The method of claim 18, wherein the target environment comprises soil, phyllosphere, rhizosphere, sewage reclamation, toxic spill, fermentation, or the gastrointestinal tract.

20. The dehydrated composition of 33, wherein the encapsulated microorganisms are present in the dehydrated composition at an initial concentration of less than 100 CFU per particle.

21. The composition of claim 1, wherein, following fluid absorption, the microorganisms are released into the environment within up to 7 days.

* * * * *